United States Patent [19]

Truex et al.

[11] Patent Number: 4,934,366

[45] Date of Patent: Jun. 19, 1990

[54] FEEDTHROUGH CONNECTOR FOR IMPLANTABLE MEDICAL DEVICE

[75] Inventors: Buehl E. Truex, Glendora; William H. Stutz, Jr., Burbank, both of Calif.

[73] Assignee: Siemens-Pacesetter, Inc., Sylmar, Calif.

[21] Appl. No.: 409,202

[22] Filed: Sep. 19, 1989

Related U.S. Application Data

[63] Continuation-in-part of Ser. No. 240,895, Sep. 1, 1988, abandoned.

[51] Int. Cl.⁵ ............................................. A61N 1/375
[52] U.S. Cl. .................................. 128/419 P; 128/786
[58] Field of Search .................. 128/419 P, 784, 785, 128/786; 439/353, 668, 669, 840

[56] References Cited

U.S. PATENT DOCUMENTS

| | | | |
|---|---|---|---|
| 3,683,932 | 8/1972 | Cole | 128/419 P |
| 3,760,332 | 9/1973 | Berkovits et al. | 128/419 P |
| 3,871,382 | 3/1975 | Mann | 128/419 P |
| 4,142,532 | 3/1979 | Ware | 128/419 P |
| 4,154,248 | 5/1979 | Jones | 128/419 P |
| 4,182,345 | 1/1980 | Grose | 128/419 P |
| 4,316,471 | 2/1982 | Shipko et al. | 128/419 P |

OTHER PUBLICATIONS

"Implants for Surgery-Cardiac Pacemakers-Part 4: Low Profile Connector For Implantable Pacemakers", IEC SC62D/WG6; ISO TC150/SC2WG2; M. Bilitch, M.D., Chairman, (Jul. 1987).

Voluntary Standard VS-1, Final Draft, (Jun. 2, 1986).

*Primary Examiner*—Lee S. Cohen
*Assistant Examiner*—S. Getzow
*Attorney, Agent, or Firm*—Malcolm J. Romano

[57] ABSTRACT

A feedthrough connector for an implantable medical device, combines the connector function with the feedthrough function and eliminates the need for the cast epoxy connector previously used on such devices. The feedthrough connector includes a barrel assembly having open and closed ends. The open end of the assembly has an opening for receiving a slidably inserted electrical lead. The barrel assembly includes cylindrical metal conductive portions separated by cylindrical ceramic insulating portions. Spring contacts are mounted on the inside of the metal portions and are adapted to make electrical contact with the appropriate contacts of an electrical lead when the lead is inserted into the connector. The outer side of the metal portions are electrically connected to the appropriate electrical circuit within the housing, and the open end of the barrel assembly is bonded (welded) to the device housing so that the inside of the device can be hermetically sealed. Releasable lead gripping means are included as part of the barrel assembly to detachably lock and seal the electrical lead in its inserted position inside of the connector.

32 Claims, 6 Drawing Sheets

FIG_8A

FIG_8B

FIG_9A

FIG_9B

FEEDTHROUGH CONNECTOR FOR IMPLANTABLE MEDICAL DEVICE

This is a continuation-in-part of copending application(s) Ser. No. 07/240,895 filed on Sept. 1, 1988, now abandoned.

The present invention relates to an electrical connector used with an implantable medical device, such as a pacemaker, for connecting an implantable electrical lead to the electrical circuits within a hermetically sealed housing of the medical device. More particularly, the present invention relates to a feedthrough/connector for use with a sealed implantable pacemaker that combines the connector function with the feedthrough function and that eliminates the need for the cast or other preformed epoxy connector that has heretofore been used on implantable pacemakers.

BACKGROUND OF THE INVENTION

Modern pacemakers monitor the activity of a heart and provide a stimulation pulse in the absence of normal heart activity. Advantageously, such devices are relatively small, light-weight and implantable. In order to sense and stimulate the heart, however, such pacemakers must be used with a pacemaker lead—an electrical conductor that carries electrical signals between the heart and the pacemaker. Advantageously, the pacemaker lead can be inserted into the heart transvenously through a relatively simple and well-known surgical procedure. Disadvantageously, one end of the lead (designated herein as the "connecting end") must be electrically and mechanically secured to the pacemaker in a way that provides for a long-term safe and secure, yet detachable, connection. Those skilled in the pacemaker art have long sought for a simple, yet reliable and safe, means for making this detachable electrical and mechanical connection between the pacemaker device and the connecting end of the pacemaker lead.

Figures 1, 2, 3A, 3B, 5:
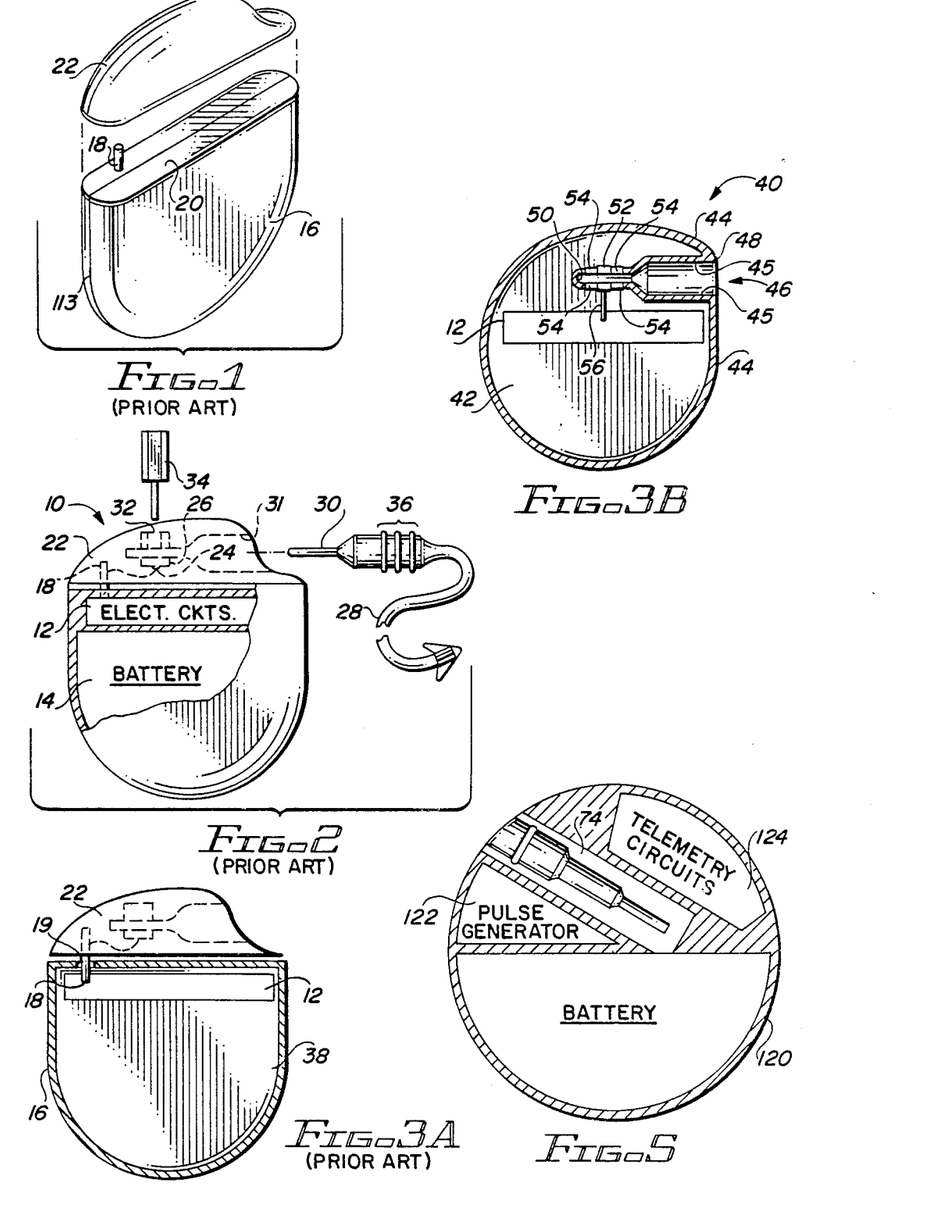
FIG. 1 is an exploded view of a prior art pacemaker, showing the sealed pacemaker housing 16 and its cast epoxy connector top 22.
FIG. 2 is a a partial cutaway side view of a prior art pacemaker, showing the assembled relationship between the main components thereof.
FIGS. 3A and 3B conceptually compare the layout and hermetically sealed area of a prior art pacemaker (FIG. 3A) and the pacemaker of the present invention (FIG. 3B)
FIG. 5 is a view as in FIG. 4 of an alternative arrangement of the main components of the invention.

In order to appreciate the advantages of the present invention, it will help first to have a basic understanding of the manner in which the mechanical and electrical connection functions are carried out in prior art pacemakers. The main components associated with the connection function of known prior art pacemakers are shown in FIGS. 1 and 2. A pacemaker 10 electrically includes a battery 14 that powers electrical circuits 12. The pacemaker electrical circuits 12 and battery 14 are mechanically housed and hermetically sealed in a suitable housing 16. Typically, this housing or case 16 is shaped to include a flat side or platform 20 to which a suitable epoxy connector 22 can be bonded. At least one feedthrough terminal 18, in electrical contact with the electrical circuits 12, passes through the case or housing 16 and protrudes out from the platform 20. This feedthrough terminal 18 is electrically isolated from the case 16. A platinum wire 24, or other suitable conductive element, connects the terminal 18 to a conductive connector block 26 that is fitted within the connector 22. A pacemaker lead 28, having a proximal electrode 30, connects to the pacemaker electrical circuits by inserting the proximal electrode 30 into a receiving channel 31 of the connector 22 until the electrode 30 is in contact with the connector block 24. A set screw 32 is then securely tightened using a torque wrench 34 to firmly hold the electrode 30 in both mechanical and electrical connection with the connector block 26. A septum (not shown) is typically placed over the set screw 32 in order to prevent body fluids from seeping through the set screw hole. Further, sealing ribs or ridges 36 on the connecting end of the pacemaker lead are designed to tightly engage the inside edges of the receiving channel 31 in order to prevent any body fluids from entering into the receiving channel 31 once the connecting end of the lead has been pushed into the connector 22.

Representative descriptions of many of the features and functions of prior art pacemaker connection systems may be found in U.S. Pat. Nos.: 3,683,932; 3,760,332; 4,142,532; 4,154,248; 4,182,345; and 4,316,471. While that which is described in these prior patents Varies greatly relative to, for example, different types of locking mechanisms for performing the mechanical connection function, or different types of arrangements for performing the electrical feedthrough function, including the use of bipolar or multiple connector leads, all such systems include the use of a premolded or cast connector 22 that is bonded to a sealed pacemaker housing 16 in which the electrical circuits are located.

Typically, prior art connectors 22 are cast in place from epoxy to the platform or header 20 of the pacemaker, or a premolded connector is bonded to the platform 20 using a suitable sealing and bonding agent. Further, once the electrical connection is made from the terminal post 18 to the connector block 26, and the connector is attached to the housing, all remaining voids within the connector 22, not including the receiving channel 31 into which the proximal end of the lead is to be inserted, must be filled with a suitable filler material, such as a two-component epoxy or silicone rubber.

As is evident from the above description, placing a connector on a pacemaker housing is a very labor-intensive process involving many components. What is needed is a simpler manner of lead attachment that provides the requisite mechanical and electrical connection functions using fewer components and less labor yet providing higher reliability. The present invention addresses these and other needs.

SUMMARY OF THE INVENTION

The present invention provides a feedthrough connector for a pacemaker, or other implantable medical device, that advantageously combines the connector function with the feedthrough function and eliminates the need for the cast epoxy connector previously used on prior art pacemakers. Eliminating the external cast epoxy connector advantageously eliminates the need for septums, setscrews, and the feedthrough terminal and its associated platinum wires and connector blocks, as well as the whole time consuming casting process with its inherent propensity for cosmetic problems.

The feedthrough/connector of the present invention includes a barrel assembly having an open end and a closed end. The open end of the assembly provides an opening into which the connecting end of a pacemaker lead, or other electrical lead, can be inserted. The barrel assembly includes metal (conductive) portions separated by ceramic (nonconductive) insulating portions. An overlap region of the conductive portions, separated by the nonconductive portion, advantageously provides structural strength as well as a capacitor structure. This capacitor helps filter out unwanted electromagnetic interference (EMI) signals from passing through the connector. Spring contacts are mounted on the inside of the metal portions and are adapted to make electrical contact with the appropriate electrodes of the pacemaker or other electrical lead when the connecting end of the lead is inserted into the connector.

During assembly of the pacemaker or other device, the barrel assembly is fitted into an opening in the device housing with the open end being flush with the surface of the housing and the closed end protruding into the housing. The outer side of the metal portions are electrically connected to the appropriate electrical circuit within the housing, and the open end of the barrel assembly is welded or otherwise bonded to the device housing so that the inside of the device can be hermetically sealed. Releasable lead gripping means are included as part of the barrel assembly to detachably lock and seal the connecting end of the electrical lead in its inserted position inside of the connector.

It is a feature of the present invention to provide a feedthrough/connector system that eliminates the need for the cast epoxy type of connectors used in prior art pacemakers, and the multiplicity of problems and costs associated with the use of such cast connectors.

It is a further feature of the invention to provide a pacemaker or other implantable medical device that can be made from fewer components and that provides the requisite mechanical and electrical feedthrough functions at lower cost and higher reliability than prior art connection systems.

Still a further feature of the present invention is to provide a pacemaker that can be smaller than pacemakers of the prior art that perform an equivalent function.

Yet a further feature of the present invention is to provide a connection system for use with an implantable medical device, such as a pacemaker, that firmly yet detachably locks and seals the connecting end of an electrical lead thereto but that does not require the use of setscrews, septums, or equivalent mechanical securing and sealing devices.

A still further feature of the present invention is to provide a connection system for use with implantable medical devices that is compatible with existing electrical leads, whereby a medical device having the connection system of the present invention may replace a prior art system and still utilize an existing implantable or implanted lead that was used with the prior art system.

BRIEF DESCRIPTION OF THE DRAWINGS

The above and other features and advantages of the present invention will be more apparent from the following more particular description thereof, presented in conjunction with the following drawings, wherein.

DETAILED DESCRIPTION OF THE INVENTION

The following description presents the best contemplated mode for practicing the invention. This description is not to be taken in a limiting sense but is made merely for the purpose of describing the general principles of the invention. The scope of the invention should be ascertained with reference to the appended claims.

The present invention is best understood with reference to the drawings, wherein like numerals are used to represent like parts or elements throughout. Where elements in one figure are similar to elements of another figure, but not the same as, such elements may be referred to using a modified reference numeral, e.g., 72' or 72" instead of 72.

FIGS. 1 and 2 have been described previously in connection with the description of the prior art in the Background portion of this application. FIG. 3A likewise depicts a prior art pacemaker device. FIG. 3A shows the relative size of the device and area therewithin that is hermetically sealed. The sealed area is the shaded area 38. As has been indicated, the electrical circuits 12 of the pacer are housed in the sealed area 38. In order to make electrical contact with these circuits 12, at least one feedthrough terminal 18 must pass through the case 16. Some type of insulating material 19 must be used with the feedthrough terminal 18 in order to electrically insulate this terminal from the case 16. (A portion of the case 16 typically functions as a return electrode for unipolar pacing.) A more complete description of one particular type of feedthrough terminal 18 can be found in one of applicants' copending applications, Ser. No. 07/161,700, filed 01/29/88. Further, more detail concerning one type of prior art connector 22 can be found in another of applicants' copending patent applications, Ser. No. 07/013,747, filed 02/12/87.

FIG. 3A should be compared to FIG. 3B, where there is shown a simplified side sectional view of a pacemaker 40 incorporating the present invention. In FIG. 3B, that portion of the pacemaker that is hermetically sealed is the shaded area 42. This area is enclosed by the case 44 of the pacemaker. As with the prior art device, this sealed area 42 includes the electrical circuits 12 of the pacer. Unlike the prior art device, a receiving channel 46 protrudes inwardly into the pacer. This channel may conceptually be thought of as an indented channel for it includes an open end 48 flush with the surface of the pacer housing 44 and a closed end 50 within the pacer housing 44, thereby forming, as it were, a long narrow indent within the pacer housing 44. (As will be described more fully below, the receiving channel 46 is not formed by indenting the pacer housing 44. Nonetheless, for purposes of illustrating those areas of the pacer that are sealed from those areas that are not, it may be helpful to conceptualize the receiving channel as an indented channel.) The inside walls 45 of the receiving channel 46 are not included within the sealed areas of the pacemaker 40 for they are open to the outside environment of the pacer through the open end 48. In contrast, the reverse side of the inside walls 45 of the receiving channel 46 (referred to hereafter as the "backside" or "outside" walls of the receiving channel 46) are exposed to the sealed inner portions of the pacemaker.

Still referring to FIG. 3B, a portion 52 of the walls of the receiving channel 46 are made from a conductive material, such as a short 316L stainless tubular section. This conductive portion is insulated from the pacer walls 44 by insulating (nonconductive) portions 54 of the walls of the receiving channel 46 which are adjacent the conductive portion. Typically, as is explained more fully below, these nonconductive portions 54 may be made from short ceramic tubular sections that are hermetically bonded to the conductive portion 52 and the walls of the channel 45. However, any suitable nonconductive material, such as an epoxy or polymer substance, could be used to perform this insulating function providing that a suitable hermetic bond is made thereto.

The backside or outside of the conductive portion 52 is electrically connected to the pacemaker circuits 12 by means of a suitable electrical conductor 56. Advantageously, because the conductor 56 is only included within the sealed portion 42 of the pacer, it can be made from any suitable electrically conductive material, not just those types of conductors (such as titanium) that are compatible with exposure to body fluids. However, the conductor 56 should be made from a material that is compatible with the type of material used for the conductive portion 52 of the receiving channel 46 in order to prevent any galvanic or other adverse reactions between dissimilar metals in electrical contact with each other.

Figures 4, 6B:
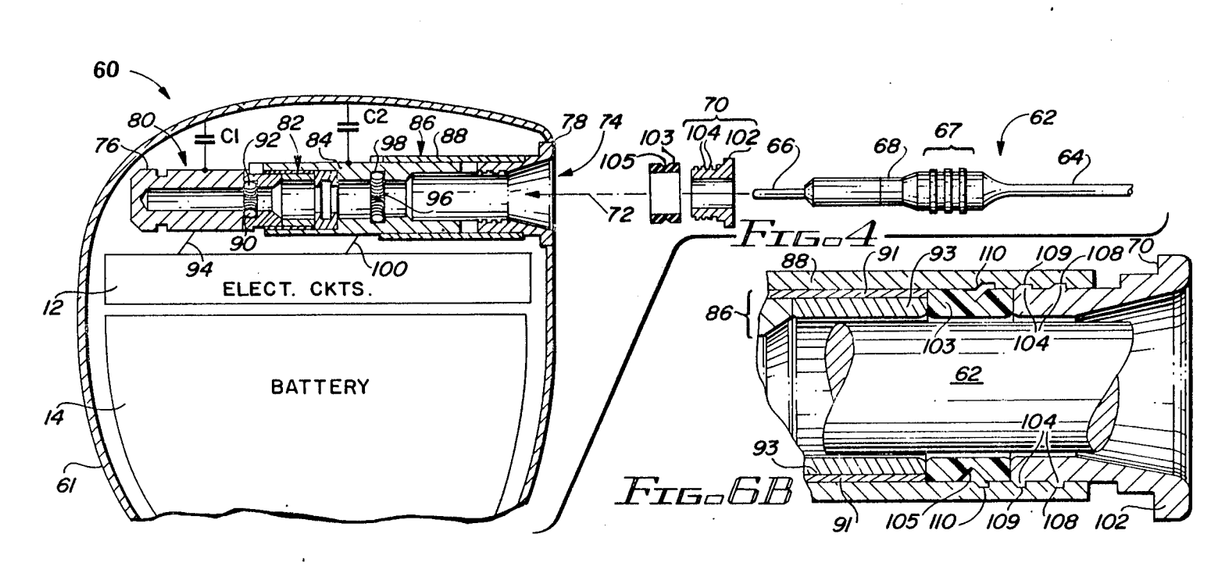
FIG. 4 is a partial cutaway and exploded side view of a pacemaker having the feedthrough/connector of the present invention, showing the relationship between the main components thereof.
FIGS. 6A and 6B are partial side views of the barrel assembly of the present invention showing the connector in its closed or locked position (FIG. 6A), and its open position (FIG. 6B)
Figure 6A:
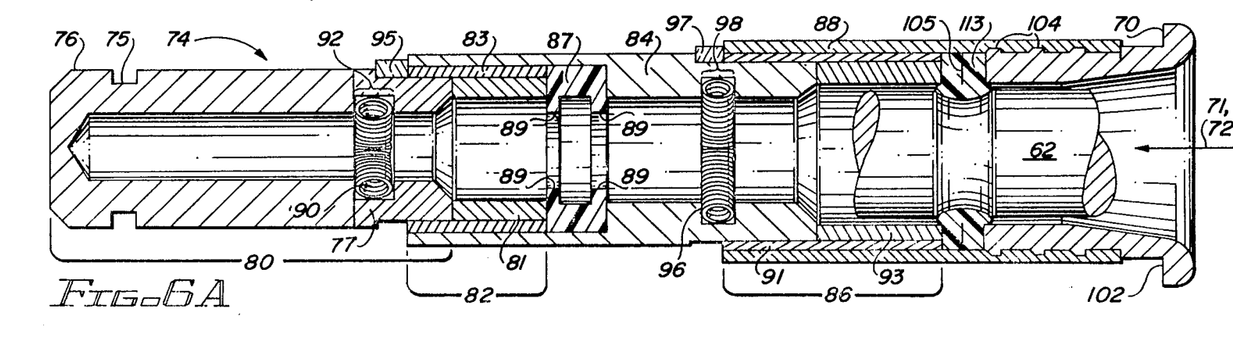

Referring now to FIGS. 4, 6A and 6B, a more detailed cutaway side and sectional views of a pacemaker 60 embodying the present invention is shown. Included in FIG. 4 is a side view of the connecting end 62 of a pacing lead 64 adapted to be inserted into the connector of the present invention, as well as a sectional side view of a lead lock button 70 and sealing/gripping element 103. (For clarity, the lead lock button is shown in FIG. 4 in an exploded position from its normal position within the open end of the receiving channel 72 of the connector.) The lead lock button 70 and sealing/gripping element 103 lock and seal the connecting end 62 of the lead 64 into a receiving channel 72 of the feedthrough connector. It is noted that the lead 64 shown in FIG. 4 is a bipolar lead, having a connecting end tip electrode 66 and a connecting ring electrode 68, both of which electrodes must make electrical contact with the electrical circuits 12 of the pacemaker 60. It is further noted that in recent years there has been an effort underway in the pacemaker industry to voluntarily standardize pacemaker connectors, at least insofar as the size, spacing, and shape of the connecting end of the pacing lead is concerned, thereby allowing an implanted lead in a patient to be used with any manufacturer's pacemaker. That which is shown as the proximal end 62 in FIG. 4 is intended to depict that which is known as a voluntary standard VS-1A lead. The VS-1A lead is a bipolar lead having specific dimensions. The specifications associated with the VS-1A connecting end may be found in public domain documents, such as IEC SC62D/WG6 and ISOTC150/SC2/WG2 (July 1987); and Voluntary Standard VS-1 (June 1986), which documents are incorporated herein by reference. Other standardized connecting ends include the VS-1 lead and VS-1B lead. One of the advantageous features of the feedthrough connector described herein is that it is compatible for use with all of these industry standard pacing lead connectors. Another desired feature of the invention allows the connecting end 62 of the lead to be slidably inserted into the connector without having to rotate either the lead or the case relative to each other, which rotation (typically involving a plurality of turns, e.g., a rotation of more than 360 degrees) was required in some very early prior art pacemakers. See, e.g., U.S. Pat. No. 3,871,382.

FIGS. 4 and 6A illustrate the manner in which the feedthrough connector of the present invention is fabricated. A barrel assembly 74 is constructed which, when assembled, defines the receiving channel 72. The barrel assembly is shown in its inserted position within a pacemaker housing in FIG. 4. The barrel assembly is shown by itself in an enlarged view in FIG. 6A in order to better illustrate some of the details associated therewith. The barrel assembly 74 includes tubular sections of conductive and nonconductive materials that are hermetically joined together. A blind hole end piece 76 closes one end of the assembly, and the opposite end 78 is welded to the device housing 61. A first conductive section 80 of the barrel assembly 74 includes a spring contact 90 within a groove 92. As shown best in FIG. 6A, this first conductive section 80 comprises the blind hole end piece 76 welded to an adjoining conductive section 77. A counter bore is machined into one end of the section 77. During assembly, the spring contact 90 is placed into the bore 79 prior to welding the end piece 76 to the section 77. Once this weld is completed, the groove 92 is formed (by the bore and the end of the end piece 76), which groove maintains the spring contact 90 in its desired position. Both the end piece 76 and the section 77 are preferably made from 316L stainless steel.

A second conductive section 84 of the barrel assembly 74 is bonded to the spring contact end of the first conductive section 80 by means of a first nonconductive section 82. In the preferred embodiment, the nonconductive section 82 comprises a rigid portion 81 and a seal portion 83. Preferably the rigid portion 81 is made from a hard relatively nonmelting ceramic bead or ring, and the seal portion 83 is made from Kryoflex, a form of meltable ceramic available from Kyle Technology, of Roseburg, Oreg. The seal portion 83, upon being subjected to sufficient heat for a prescribed period of time, melts and fuses with the adjacent conductive sections 77 and 84 as well as the rigid ceramic section 81 in order to form a suitable hermetic bond and seal.

A second spring contact 96 is placed within a groove 98 located around the inside of one end of the second conductive section 84. A silicone seal 87 may optionally be placed within a suitable bore at the other end of the second conductive section 84. (Besides the seal 87, the first nonconductive section 82 and a portion of the conductive piece 77 are also fitted within this same bore.) The silicone seal 87, which includes a plurality of sealing ribs 89, tightly encircles the connecting end 62 of the lead 64 when the lead is inserted into the receiving channel 72, thereby preventing body fluids from coming in contact with the first conductive section 80. As will be explained more fully hereinafter, the seal 87 provides only a passive and secondary seal for the connector. An active and primary seal is provided by the lead lock button 70 and its associated sealing/gripping element 103. For this reason, there may be some applications where the seal 87 may not be needed.

A third conductive section 88 of the barrel assembly 74 is similarly bonded to the spring contact end of the second conductive section 84 by means of a second nonconductive section 86. This second nonconductive section 86 is similar to the first nonconductive section 82 in that it comprises a rigid portion 91 and a seal portion 93, with the seal portion 93 melting and fusing with the adjacent conductive sections 84 and 88 and the rigid ceramic 93 upon being subjected to adequate heat for a prescribed time period.

As also seen in FIG. 6A, a positioning groove 75 is placed around the backside of the first conductive section 80 of the barrel assembly 74. This positioning groove 75 is used during manufacture of the pacer in order to correctly position and support the assembly within the pacemaker or other device. Further, during assembly of the barrel 74, ceramic spacer rings 95 and 97 may be optionally used around the backside of conductive sections 80 and 84, respectively, in order to assure that these conductive sections are inserted into the adjacent conductive sections the appropriate depth prior to firing the ceramic bond and seal.

In the preferred embodiment, as shown best in FIG. 6A, the conductive section 80 overlaps the conductive section 84 with the nonconductive section 82 being inserted therebetween. Advantageously, this overlap allows the mechanical strength of the conductive sections to overlap and protect the relatively weaker nonconductive sections, thus assuring that there are not weak sections of the barrel assembly that could easily break. A similar overlap occurs between the conductive section 84 and the conductive section 88, with the nonconductive section 86 being inserted therebetween.

Further, this overlap advantageously provides the structure of a capacitor. That is, a first conductive plate (e.g., one end of the conductive section 88) is uniformly spaced apart from a second conductive plate (e.g., one end of the conductive section 84) by a dielectric nonconductive material (e.g., the nonconductive section 86). These built-in capacitors (there are two such capacitors) advantageously provide an electrical filter for filtering out unwanted signals, such as EMI, from the signals present on the first and second conductive portions, 80 and 84, of the barrel assembly. Further, these built-in capacitors may be supplemented, as required, with external capacitors, such as capacitors C1 and C2 (FIG. 4), placed within the sealed portion of the pacemaker housing.

The conductive sections 80 and 84 are preferably made from 316L stainless steel. Conductive section 88 is made from titanium to facilitate welding it to the housing 61. As has been indicated, nonconductive sections 82 and 86 are preferably made from a ceramic material, including a rigid portion and a seal or meltable portion. Other suitable conductive and nonconductive materials could, of course, be used.

As already mentioned, included within the first conductive section 80 is a spring contact 90 that is fitted within a groove 92 formed within an inside wall of the section 80. This spring contact is preferably a canted coil spring, commonly referred to as a garter spring. It makes multiple electrical contacts with the conductive sections 76 and 77 around the periphery of the groove 92. Further, when the connecting end 62 of the lead 64 is inserted into the receiving channel 72, this spring 90 makes multiple electrical contacts with the connecting tip electrode 66. A suitable electrical conductor 94, in electrical contact with the back side of the conductive section 80 is also in electrical contact with the electrical circuits 12 (FIG. 4). Thus, by means of the garter spring 90, which is in electrical contact with the inside of the conductive section 80, and the conductor 94, which is in electrical contact with both the back side of the conductive section 80 and the electrical circuits 12, the connecting tip electrode 66 is placed in electrical contact with the electrical circuits 12 which are hermetically sealed in the pacemaker housing.

In a similar fashion, the second spring contact 96 is placed within a groove 98 around the inside of the second conductive section 84. The backside of this second conductive section 84 is electrically connected to the pacemaker circuits 12 by means of a second conductor 100. This second spring contact 96, which is also a canted coil spring, or garter spring, makes multiple electrical contact with the connecting ring electrode 68 of the pacing lead 64 when such lead is inserted into the receiving channel 72 of the connector.

Figure 9A:
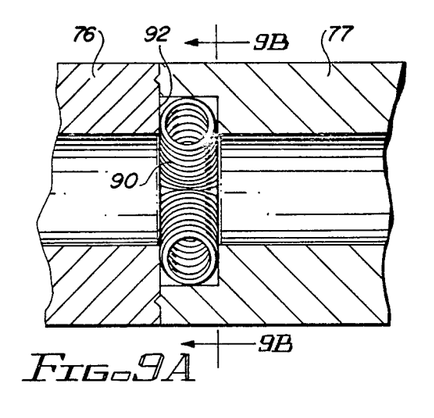
FIG. 9A is an enlarged side view of the electrical contact means used within the barrel assembly for the purpose of making multiple electrical contacts between a conductive cylindrical portion of the barrel assembly and an electrode of the pacemaker lead.
Figure 9B:
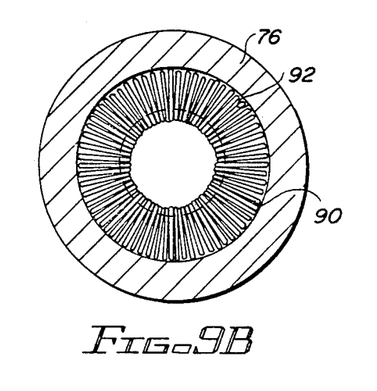
FIG. 9B is a sectional view taken along the line 9B-9B of FIG. 9A.

The garter or canted coil springs 90 and 96 comprise helically wound spring elements configured in a circle, thus forming doughnut-shaped elements. As indicated above, these springs advantageously provide multiple electrical contacts around the entire periphery of the elements with which they come in contact, as shown best in FIGS. 9A and 9B. Such garter springs are commercially available from, for example, Bal-Seal Corporation, of Santa Ana, Calif.

Still referring to FIGS. 4, 6A, and 6B, a lead lock button 70 will now be described. This button provides a mechanism for locking the connecting end 62 of the lead 64 into its desired position within the receiving channel 72 of the feedthrough connector. As is evident from the figures, the lead lock button 70 is a relative short annular element having an opening 71 through the center thereof. This opening has a diameter sufficiently large to allow the connecting end 62 of the pacemaker lead 64 to be snugly passed therethrough. The button 70 further has a circumferential lip 102 at one end thereof (used to facilitate gripping the button as it is slid between its open and locked positions in the receiving channel 72) and a plurality of small detent bumps 104 near the other end, used to hold the button in either of its two positions. A short section of tubular or annular resilient material 103, such as silicon rubber, is held captive within the receiving channel 72 when the lead lock button is inserted. This annular resilient material 103 functions much like a collar having an adjustable inner diameter. When the lead lock button is in one position, the diameter of the collar allows the electrical lead to pass therethrough. When the lead lock button is in its other position, explained below, the collar assumes a much smaller diameter that pinches the lead, thereby preventing the lead from any axial movement.

The resilient material 103 has a circumferential groove 105 on the outside diameter thereof to allow it to bulge or bend inwardly upon axial compression, as explained below. The material from which the button is made, in conjunction with the thickness of the walls of the button 70, and the plurality of detent bumps 104 (which engage circumferential grooves around the inside of the third conductive section 88) allow the button to snap into an open or locked position in much the same manner as the cap of a felt-tip pen (which includes one or more circumferential grooves) snaps on to the pen body (which includes a plurality of detent bumps).

Included around the inside circumference of the third section 88 of the barrel assembly 74 are spaced-apart grooves 108, 109 and 110. These grooves are adapted to receive the detent bumps 104 of the lead locking button 70. Once the lead locking button is slidably inserted into the receiving channel 72, the combination of detent bumps and grooves allow for two positions of the button 70: (1) a captive open position (FIG. 6B) that allows the lead 62 to freely pass into or out of the receiving channel 72; and (2) a closed position (FIG. 6A) wherein the lead 62 is locked into the receiving channel. In the open position (FIG. 6B), the detent bumps 104 engage grooves 108 and 109, thus holding the locking button captive within the connectors and the resilient material 103 is held captive between the end of the nonconductive sections 91, 93 and the end of the lead lock button 70. In this open position, the material 103 is not substantially axially compressed, and the lead 62 can pass therethrough. In the closed or locked position (FIG. 6A), the detent bumps 104 engage grooves 109 and 110, and the resilient material 103 is subjected to a significant axial compression, which compression causes it to fold or bend at the groove 105 and bulge radially inward into the receiving channel 72. This action causes the resilient material 103 to firmly grip and compress the lead 62 around its circumference, much like a shrinking collar. Advantageously, this gripping action further provides an active (under pressure) seal that totally and completely blocks the entry of any body fluids into the receiving channel 72.

In the preferred embodiment, the resilient tubular material 103 is a noncompressible elastomer, such as silicone or urethane. The gripping action on the lead locking button 70 places the elastomer of the lead lock mechanism in firm contact with the silicon rubber of the pacing lead. As has been indicated, this action not only provides a very effective (tight) and active (under pressure) seal, but it also provides a very firm grip or lock because of the high coefficient of friction of these materials. The lead locking button 70 is preferably made from a nonconductive biocompatible thermoplastic resin, such as polysurfone or nylon.

It is also noted that sealing ridges 67 placed around the circumference of the connecting end 62 of the lead 64 in accordance with the VS-1A standard (or other standards) are tightly received within the opening 71 of the lead lock button 70 and/or the receiving channel 72. These ridges provide a secondary or back-up passive seal that further prevents any body fluids from entering the channel 72, just as do the silicone seal ridges 89 previously described.

Referring back to FIG. 4, it is noted that the case 61 of the pacemaker 60 is typically assembled in halves, commonly known as clamshells, with the two halves being welded together around their periphery once all of the electrical components have been placed therein. (The welding seam for a prior art pacemaker, for example, is shown as 113 in FIG. 1) In accordance with the present invention, such assembly techniques can continue to be used. That is, once the barrel assembly 74 has been assembled, it is positioned within a suitable opening within that half of the pacemaker 60 containing the other electrical components (circuits 12 and battery 14). After the appropriate electrical connections are made between the backside of the conductive elements 80 and 84 and the electrical circuits 12, and after the filter capacitors C1 and C2 are installed (if such are used), and after other conventional assembly steps are completed, the other half of the pacemaker case is welded or otherwise hermetically bonded to the half of the pacemaker case containing all of the pacemaker elements, and the open end 72 of the barrel assembly 74 is welded or otherwise bonded to both pacemaker case halves, in order to hermetically seal the entire pacemaker case. In a preferred assembly process, the hermeticity of the barrel assembly provides a measured leak rate of no greater than $2 \times 10E-9$ atm-cc/sec of air, when tested in accordance with MIL-STD-883, method 1014, condition A. The hermeticity of the pacer assembly may be somewhat less than this (i.e., a slightly higher measured rate of leakage) due to the aging of the barrel assembly, which aging may degrade the hermeticity level somewhat. For example, a hermeticity level for the pacer assembly of $2 \times 10E-8$ atm-cc/sec would be acceptable.

Figure 7A:
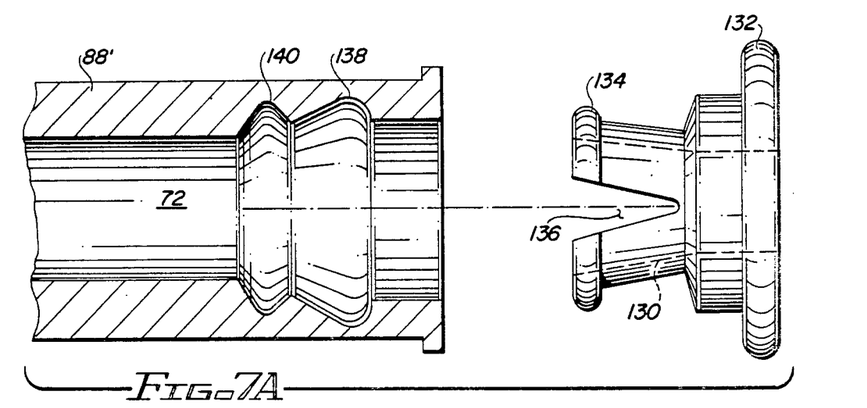
FIGS. 7A-7D are side sectional views (FIGS. 7A, 7C, 7D) and an end view (FIG. 7B) of an alternative embodiment of the barrel assembly of the present invention wherein a collet is used as the locking means.
Figure 7B:
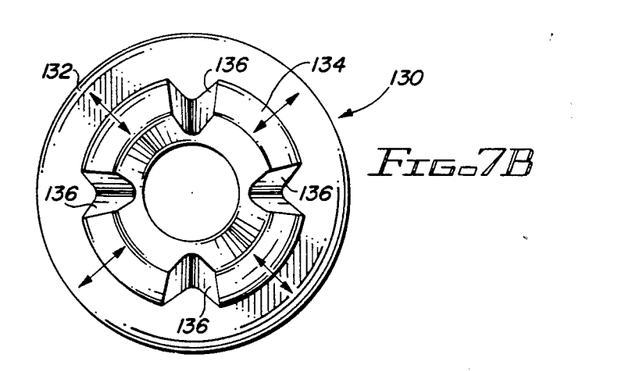
Figure 7C:
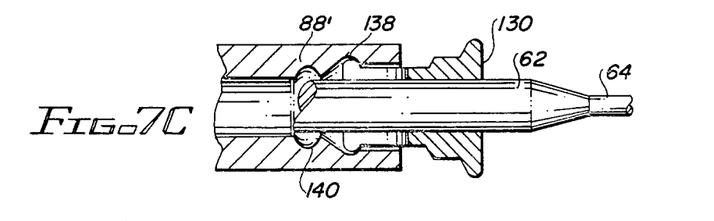
Figure 7D:
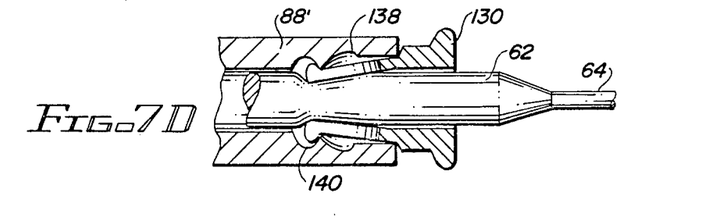

Referring next to FIGS. 7A-7D, an alternative embodiment of the lead locking means of the present invention is illustrated. As shown best in FIGS. 7A and 7B, this embodiment utilizes a collet 130 that is adapted to be slidably inserted into the receiving channel 72' of the feedthrough connector. The collet 130 includes a circumferential lip 132 (used to help push the collet into and pull the collet out of the receiving channel 72') and an engaging detent rib 134 Four slits 136, uniformly spaced around the periphery of the body of the collet, allow the detent rib 134 to be radially compressed. However, the material from which the collet is made, e.g. an engineering biocompatible thermoplastic resin (such as polysurfone or nylon), provides a spring bias that tends to force the rib 134 in an outwardly radial direction. Receiving grooves 138 and 140 in the third section 88' of the barrel assembly are designed to receive the rib 134 as the collet 130 is pushed into the receiving channel. The diameter of the first groove 138 is larger than the diameter of the second groove 140. Hence, when the detent rib 134 is received in the first groove 138, the collet has not been compressed to the point where the lead 64 cannot pass therethrough. Thus, with the detent rib 134 residing in the first groove 138, the collet is in its "open" position, and the lead 64 can be inserted into the receiving channel 72' of the connector. This open position is illustrated in FIG. 7C. Note that the collet 130 is held captive within the connector in this open position, thereby preventing the collet from becoming misplaced. However, when the collet 130 is further slid into the receiving channel 72', such that the detent rib 134 engages the second groove 140, the collet is compressed to the point where it squeezes the body of the connecting end 62 of the lead 64 and firmly locks the lead into its inserted position. Thus, with the detent rib 134 residing in the second groove 140, the collet is in its "locked" position and the lead can not be removed from the connector. This locked position is shown in FIG. 7D. The lead is released by using a suitable tool to engage the circumferential lip or rim 132 so that the collet can be pulled or slid from its "locked" position to its "open" position.

Figure 8A:
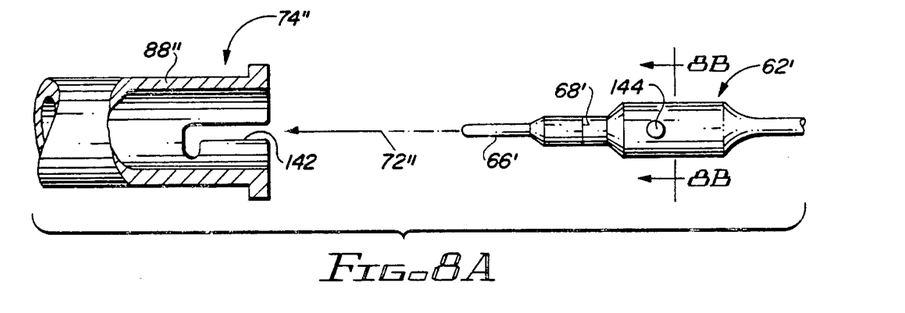
FIG. 8A is a side cutaway view of still an additional alternative embodiment of a portion of the barrel assembly of the present invention wherein a twist-locking bayonet-type mechanism is used to lock the lead into its inserted position within the receiving channel of the barrel assembly.
Figure 8B:
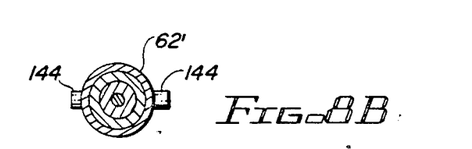
FIG. 8B is a partial sectional view taken along the line 8B-8B of FIG. 8A.

Referring next to FIGS. 8A and 8B, another alternative embodiment of the lead locking means of the present invention is shown. In accordance with this embodiment, a barrel assembly 74" includes a plurality of keyed channels 142 along the inside of a third section 88" of the barrel assembly. These keyed channels run longitudinally for a short distance and then make a right angle and run circumferentially. Protruding pins 144, or equivalent engaging elements, are placed into the proximal end 62' of the pacing lead. These pins 144 are received within the keyed channels 142 when the lead is inserted into the receiving channel 72" of the connector. Once the pins have traversed the longitudinal length of these channels 142, the lead is rotated relative to the receiving channel 72", thereby placing the pins 144 at the extreme end of the keyed channels 144. With the pins in this position, the lead cannot be longitudinally removed from the receiving channel 72". Hence, the lead is locked into the connector. Removal of the lead is accomplished by twisting the lead relative to the connector in the other direction until the pins are aligned with the longitudinal portion of the channel 142, at which time the lead can be pulled back out of the connector. This type of lead locking mechanism is commonly known as a bayonet-type engagement. Typically, less than ⅛ of a turn is required to lock or unlock the lead. This is felt to provide a significant improvement over prior art devices where the lead must be threadably inserted into a recess within the pacemaker, typically involving many turns, and always involving relative rotation between the case and lead in excess of 360 degrees.

FIG. 5 illustrates an alternative manner in which the barrel assembly 74, of the type previously described in connection with FIGS. 4 and 6A, could be used with a circular pacemaker case 120. In such an arrangement, the location of the pacemaker circuits within the housing is altered slightly in order to better utilize the available space within the device. For example, FIG. 5 depicts the pacemaker electrical circuits as being divided into two portions: the pulse generator circuits 122 and the telemetry circuits 124. Those skilled in the pacemaker art could readily divide the pacemaker circuits into these, or other, groups for the purpose of optimally utilizing the available space within the pacemaker, thereby allowing the pacemaker to be as small as possible.

Figure 10:
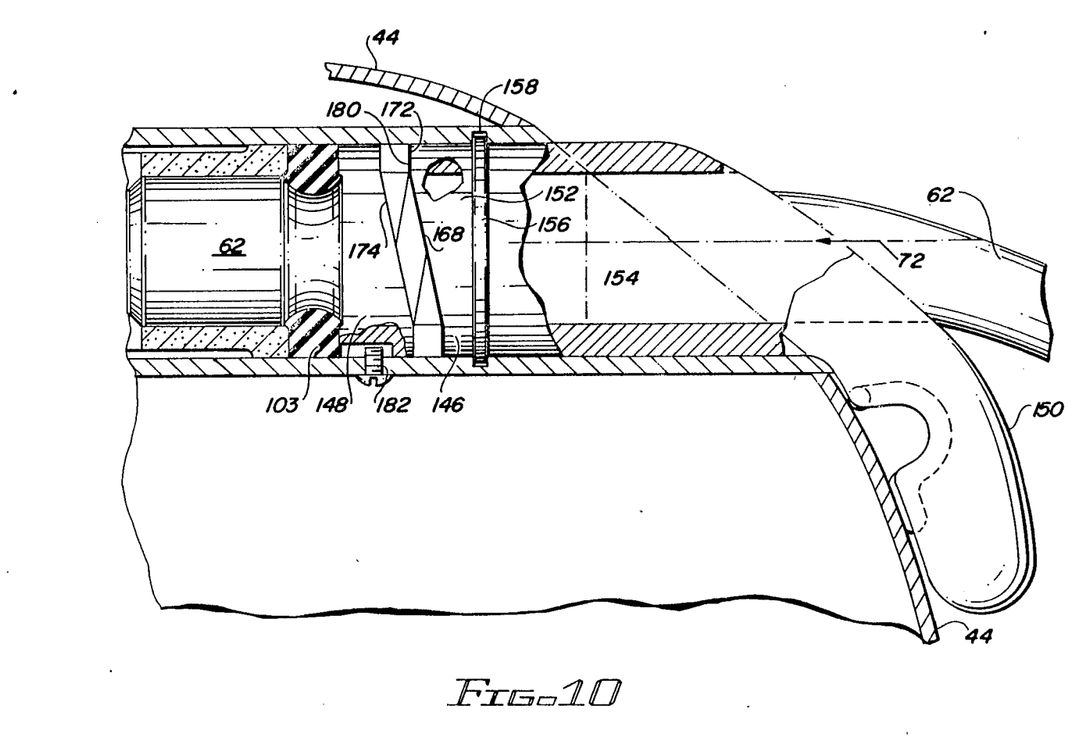
FIG. 10 is a partial cutaway perspective front view of an alternate embodiment of the locking means of the present invention.

Referring next to FIG. 10, there is shown in partial cross-section yet another alternative embodiment of the lead locking means of the present invention. The locking means is in the form of a cam follower arrangement which includes cam 146 and cam follower 148. FIG. 10 shows the cam 146 in a second or closed position, whereby the resilient material 103 is compressed so as to achieve the pinching or gripping action previously discussed.

Figure 11:
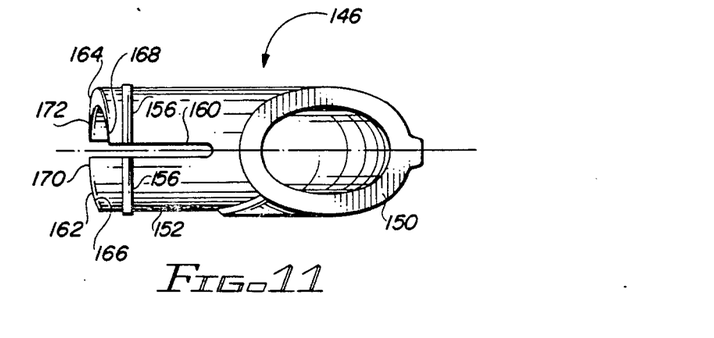
FIG. 11 is bottom view of the cam of the locking means of FIG. 10.
Figure 12A:
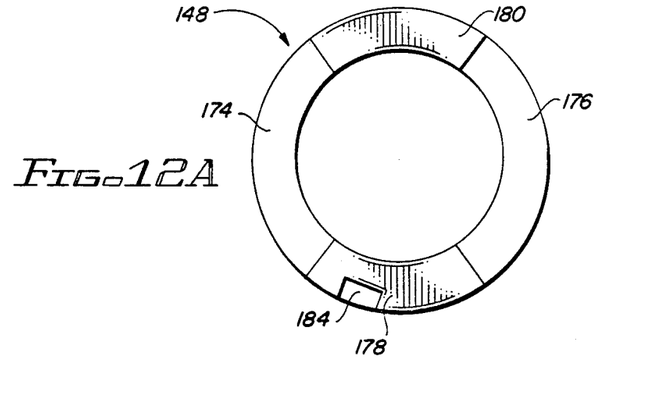
FIG. 12A is a front view of the cam follower of the locking means of FIG. 10.
Figure 12B:
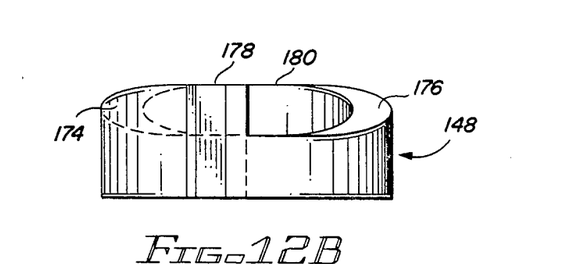
FIG. 12B is a side elevation view of the cam follower of FIG. 12A.

To better understand the functioning of the cam follower means, reference is now made to FIG. 11 and FIGS. 12A and 12B. As shown in FIG. 11, the cam 146 has a handle 150 which depends from an essentially hollow tubular portion 152. The tubular portion 152 has an inside diameter 154 sufficient in dimension to allow an electrical lead 62 to pass therethrough. Extending from the outer surface of tubular portion 152 are a pair of oppositely and outwardly facing lobes 156. The lobes 156 extend beyond the surface of tubular portion 152 sufficiently to locate within and engage an annular groove 158.

A pair of cutout channels 160 extend in an axial direction about one-half the length of the tubular portion 152. For insertion of the cam within the channel 72, the ends 162 and 164 are pinched together so that the lobes 156 are drawn sufficiently close together so that they avoid interference with the ends of channel 72, and thus are capable of being inserted in and moved along channel 72. As the cam is inserted further into the channel 72, the lobes 156 will eventually engage the end annular groove 158 and the ends 162 and 164, and due to the resiliency of the material of which cam 156 is formed, will move away from each other and resume their normal spaced-apart orientation.

When the lobes 156 are inserted in groove 158, the cam 146 is rotatable between a second or closed position as shown in FIG. 10 to a first or open position which is essentially 180 degrees away from the position shown in FIG. 10. Due to the locking or detent action of the lobes 156 and groove 158, the cam 146 is prevented from axial translation during rotation between the open and closed positions.

With further reference to FIG. 11, there is shown the curvilinear surfaces 166 and 168 on cam ends 162 and 164, respectively. Each curvilinear surface extends around respective halves of the tubular portion 152 and then terminate at respective flat land segments 170 and 172. As will be described below, the curvilinear surfaces 166 and 168 engage corresponding curvilinear surfaces on the cam follower 148 to force the cam follower in contact with material 103 to effect the desired locking and gripping action on the electrical lead 62.

Referring now to FIG. 12A and FIG. 12B, cam follower 148 includes curvilinear surfaces 174 and 176 which engage surfaces 168 and 166, respectively, of the cam 146. Curvilinear surfaces 174 and 176 terminate at flat land portions 178 and 180, respectively. Anti-rotation pin 182 extends radially from the inner surface of tubular portion 152. Pin 182 is of conventional design and is hermetically sealed in place by means of resistance-welding. Longitudinal groove 184 extends along the outer surface of the cam follower 148 in an axial direction. The cam follower 148 is inserted in the channel 7 2, such that pin 182 extends into groove 184, and the curvilinear surfaces face toward the open end of channel 72. By virtue of pin 182, the cam follower 148 is confined to axial translation only.

When the cam 146 is inserted into the channel 72 and oriented in the first or open position, the corresponding curvilinear surfaces of the cam and cam follower are in contact. As the cam 146 is rotated from the first toward the second position in a clockwise direction (as viewed looking into the open end of channel 72), due to the action of the curvilinear surfaces upon each other, the cam follower 148 is urged away from the cam 146 then to engage and compress material 103. As the cam 146 is further rotated to the second position, the respective flat land segments engage each other to establish a locking position. As mentioned previously, due to the engagement of lobes 156 and groove 158 during rotation of the cam 146, the cam is confined only to rotational motion, whereas the cam follower 148 is confined only to translational motion. At the second position, flat land segments 172 and 180 are in contact and flat land segments 170 and 178 are also in contact to establish a locked condition.

Although a counter-clockwise direction was described, it is to be understood that clockwise rotation with correspondingly reversed curvilinear surfaces is also contemplated by the present invention.

Furthermore, other cam follower means are also contemplated by the present invention; for example, a plurality of pins may be selected to extend into the tubular channel 72 from the inner surface thereof to engage corresponding cam grooves in the outer surface of cam 146. By this technique, a simple cam similar in design to the cam 146 with the exception of lobes 156 and cutout channels 160 may be used which cooperates with the plurality of pins, such that desired rotation off the cam advances the cam toward the material 103, and upon further rotation, compresses the material 103 until the cam reaches a locked position. The cam grooves may be oriented to provide for initial engagement with the pins to provide guided axial translation inward for the cam. The groove may continue in a helical fashion around the outer surface of the cam so that rotation of the cam also results in translation of the cam inward or outward, of course, depending on the direction of rotation. The groove may end in an annular portion, such that further rotation of the cam, due to the pins being received within such annular portion, causes the cam to be locked in position.

While the invention described herein has been described with reference to specific embodiments and applications thereof, numerous variations and modifications could be made thereto by those skilled in the art without departing from the spirit and scope of the invention as claimed. Accordingly, the true scope of the invention should be determined with reference to the claims set forth below.

What is claimed is:

1. An implantable medical device comprising:
    a hermetically sealed housing;
    an electrical circuit within said housing;
    An electrical connector within said housing comprising:
        a tubular barrel assembly having an open end and a closed end, and a barrel axis passing through the open end and closed end, said open end being, attached to an exposed surface of said housing, said closed end being internal to said housing, the tubular barrel assembly creating a tubular channel that protrudes into the sealed housing, but does not break the seal of said housing, the inside of said tubular channel being open to the outside of said sealed housing through said open end, the tubular channel further comprising a plurality of conductive cylindrical portions coaxial with the barrel axis, the dimension of the diameter of successive cylindrical portions progressively decreasing from the open end to the closed end,
        means for making electrical contact between selected cylindrical portions of said tubular channel and said electrical circuit, and
        locking means for detachably locking and gripping an electrical lead axially inserted into the open end of said tubular channel in electrical contact with selected cylindrical portions of said tubular channel, said locking means being actuable with less than 360 degrees of relative rotation between said lead and said tubular barrel assembly.

2. The implantable medical device of claim 1 wherein said hermetically sealed housing shall not exhibit a leak rate of greater than $2 \times 10E - 8$ atmcc/sec.

3. The implantable medical device of claim 1 wherein said hermetically sealed housing comprises a pacemaker, and said electrical lead comprises a pacemaker lead adapted to connect the pacemaker to a desired tissue location.

4. The implantable medical device of claim 1 wherein said locking means is actuable with substantially no relative rotation between said electrical lead and said tubular barrel assembly.

5. The implantable medical device of claim 1 wherein successive ones of the plurality of conductive cylindrical portions are separated by an insulating nonconductive cylindrical portion.

6. The implantable medical device of claim 5 wherein successive conductive cylindrical portions of said barrel assembly are spaced apart and overlap at their respective adjacent ends, thereby defining a region of overlap therebetween, the insulating nonconductive cylindrical portions being disposed throughout the region of overlap between successive conductive cylindrical portions, said ends of said conductive cylindrical portions being thereby held in a spaced-apart nontouching and electrically isolated relationship by said insulating nonconductive cylindrical portions.

7. The implantable medical device of claim 5 wherein said means for making electrical contact comprises:
    a canted coil spring positioned on the inside of said selected cylindrical portions so as to make electrical contact therewith in a multiplicity of locations; and
    wire means for making electrical contact with the outside of said selected cylindrical portions and said electrical circuit.

8. The implantable medical device of claim 1, wherein said locking means comprises:
    engaging means on the inside of said tubular channel;
    a cam and cam follower each having a hollow essentially tubular coaxial portion having a diameter that allows said electrical lead to pass therethrough, said cam rotatable between first and second positions, the cam having detent means being received by the engaging means for preventing axial translation of the cam, the cam follower engaging the cam such that as the cam is rotated from the first to the second position, the cam follower moves away from the cam in an axial direction; and
    gripping means for engaging the cam follower and for gripping said electrical conductor whenever the cam is rotated from the first to the second position and for releasing said electrical lead whenever the cam is rotated from the second to the first position.

9. The implantable medical device of claim 8, wherein the engaging means comprises an annular groove and the detent means comprises at least one lobe protruding from an outer surface of the cam, said at least one lobe adapted to be received within the annular groove to confine the cam to rotational motion when the at least one lobe is received within the groove.

10. The implantable medical device of claim 9, comprising:
pin means extending radially from an inside surface of said tubular channel; and
groove means extending in an axial direction on an outer surface of the cam follower for engaging the pin means for confining the cam follower to translational motion in an axial direction.

11. The implantable medical device of claim 9, wherein the cam and cam follower each have corresponding matching and engaging curvilinear portions and flat land portions, such that during rotation of the cam from the first to the second position, the cam follower engages the cam initially along the respective curvilinear portions and then along the respective flat land portions, whereby when the cam and cam follower are engaged along their respective flat land portions the cam and cam follower remain in a relatively locked position.

12. The implantable medical device of claim 11, wherein the at least one lobe comprises a pair of opposite and outwardly facing lobes.

13. The implantable medical device of claim 1, wherein the locking means further comprises:
cam follower means movable axially inward toward the closed end of the tubular barrel assembly in response to rotation of the cam follower means from a first to a second position; and
gripping means for engaging the cam follower means and for gripping said electrical connector, whenever the cam follower means is rotated from the first to the second position.

14. The implantable medical device of claim 13, wherein when the cam follower means is in the second position, the cam follower means is in a locked condition.

15. The implantable medical device of claim 1 wherein said locking means comprises engaging means on the inside of said tubular channel that mate with matching engaging means on said electrical lead whenever a proximal end of said electrical lead is inserted into the open end of said tubular channel.

16. The implantable medical device of claim 15 wherein said engaging means of said tubular channel and said electrical lead become lockably engaged so as to prevent removal of said electrical lead from said tubular channel whenever said electrical lead is rotated relative to said tubular channel a fraction of a turn.

17. An implantable medical device comprising:
a hermetically sealed housing;
an electrical circuit within said housing;
a connector within said housing comprising:
an electrical tubular barrel assembly having an open end and a closed end, said open end being attached to an exposed surface of said housing, said closed end being internal to said housing, the tubular barrel assembly creating a tubular channel that protrudes into the sealed housing, but does not break the seal of said housing, the inside of said tubular channel being open to the outside of said sealed housing through said open end,
means for making electrical contact between a selected first portion of the inside of said tubular channel and said electrical circuit, and
locking means for detachably locking and gripping an electrical lead inserted into the open end of said tubular channel comprising:
engaging means on the inside of said tubular channel;
a cam and cam follower each having a hollow essentially tubular coaxial portion having a diameter that allows said electrical lead to pass therethrough, said cam rotatable between first and second positions, the cam having detent means being received by the engaging means for preventing axial translation of the cam, the cam follower engaging the cam such that as the cam is rotated from the first to the second position, the cam follower moves away from the cam in an axial direction; and
gripping means for engaging the cam follower and for gripping said electrical connector whenever the cam is rotated from the first to the second position and for releasing said electrical lead whenever the cam is rotated from the second to the first position.

18. An implantable medical device comprising:
a hermetically sealed housing;
an electrical circuit within said housing;
a connector within said housing comprising:
a tubular barrel assembly having an open end and a closed end, said open end being attached to an exposed surface of said housing, said closed end being internal to said housing, the tubular barrel assembly creating a tubular channel that protrudes into the sealed housing, but does not break the seal of said housing, the inside of said tubular channel being open to the outside of said sealed housing through said open end,
means for making electrical contact between a selected first portion of the inside of said tubular channel and said electrical circuit, and
locking means for detachably locking and gripping an electrical lead inserted into the open end of said tubular channel comprising:
first and second spaced-apart engaging means on the inside of said tubular channel;
a locking ring having a plurality of detent bumps, said locking ring having an inside diameter that allows said electrical lead to fit therethrough, and an outside diameter that allows said ring to be slidably inserted into the open end of said tubular channel, at least one detent bump of the locking ring being received by either said first or second engaging means depending upon the depth to which the locking ring is inserted into the tubular channel;
gripping means for gripping said electrical lead whenever said at least one detent bump is received by said first engaging means, and for releasing said electrical lead whenever said at least one detent bump is received by said second engaging means.

19. The implantable medical device of claim 18 wherein said first and second engaging means comprise first and second circumferential grooves on the inside of said tubular channel near the open end thereof; and wherein said at least one detent bump of said locking ring snaps into either said first or second groove depending upon the depth to which the locking ring is pushed into the tubular channel.

20. The implantable medical device of claim 19 wherein the tubular channel of the barrel assembly further includes stop means positioned near said first second circumferential grooves, and wherein said gripping means is held captive between said stop means and said locking ring, said gripping means comprising an annular section of resilient material, having an inside diameter that allows said electrical lead to pass therethrough when said resilient material is not subjected to axial compression, and further wherein said resilient material is placed under axial compression when said at least one detent bump is received within said second groove, said axial compression causing the resilient material to bulge inwardly into the tubular channel, thereby reducing the inside diameter of said annular resilient section, sufficiently to firmly grip the electrical lead thereby preventing axial movement thereof.

21. The implantable medical device of claim 17 wherein the diameter of the first groove is larger than the diameter of the second groove, and wherein the locking ring comprises a radially compressible collet, said collet having a first inside diameter that allows said electrical lead to slidably pass therethrough when the shoulder of the collet is received within said first groove, and wherein said collet has a second inside diameter that lockably grips said electrical lead when the shoulder of the collet is received within the second groove.

22. An internal connector for use with a sealed implantable medical device comprising:
  lead receiving means for slidably receiving a connecting end of an electrical lead, said lead receiving means defining an open channel within said medical device, the open channel having an open end for receiving the electrical lead, and a closed end that is not open to an inner sealed portion of said medical device, the connecting end of said electrical lead being slidably received within said open channel without breaking the seal of said medical device, the open channel comprising a plurality of spacedapart successively and axially disposed electrically conductive channel segments for making electrical contact with respective portions of an electrical lead inserted within the internal connector, the channel segments being cylindrical, the diameter of successive channel segments progressively decreasing from the open end to the closed end; and
  electrical feedthrough means for making electrical contact between the sealed inner portion of said medical device and the non-sealed open channel of said lead receiving means.

23. The connector of claim 22 wherein said feedthrough means comprises means for making electrical contact with at least one of said electrically conductive channel segments.

24. The connector of claim 23 wherein said means for making electrical contact includes multiple contact spring means positioned around the inside circumference of at least one of said electrically conductive channel segments for making electrical contact with a multiplicity of locations within said at least one electrically conductive channel segment, and electrical conductor means for making electrical contact with at least one location on the outside of said at least one electrically conductive channel segment.

25. The connector of claim 23 wherein said lead receiving means further includes at least one cylindrical channel segment separating said electrically conductive channel segments thereby electrically isolating them one from the other.

26. The connector of claim 25 wherein said cylindrical channel segment comprises a ceramic segment that is hermetically bonded to the adjoining electrically conductive channel segments.

27. An internal connector for use with a hermetically sealed implantable device comprising:
  lead receiving means for slidably receiving a connecting end of an electrical lead, said lead receiving means defining an open channel within said device that is not open to an inner sealed portion of the device;
  electrical feedthrough means for making electrical contact between the sealed inner portion of said device and a portion of the nonsealed open channel of said lead receiving means; and
  releasable lead gripping means for detachably locking the electrical lead in an inserted position inside of said lead receiving means for sealing the open channel to prevent fluids from entering therein comprising:
  lead locking means slidably received within said internal connector;
  means for engaging said lead locking means in first and second positions; and
  collar means within said lead receiving means and coupled to said lead locking means for providing a first diameter collar when said lead locking means is engaged in the first position, and for providing a second diameter collar when said lead locking means is engaged in the second position, said first diameter collar having a first inside diameter that allows said electrical lead to slidably pass therethrough, and said second diameter collar having an inside diameter that is smaller than the diameter of said electrical lead, the second diameter collar thereby pinching said electrical lead and preventing further axial movement thereof.

28. The internal connector of claim 27 wherein said collar means comprises an annular section within said lead receiving means that assumes said first diameter when said annular section is not placed under axial compression, and that assumes said second diameter when said annular section is placed under axial compression.

29. The internal connector of claim 28 wherein said annular section is held captive between said lead locking means and a stop element within said lead receiving means when said lead locking means is in said first position, and wherein said annular section is axially compressed between the stop element and the lead locking means when said lead locking means is in said second position.

30. A method of making electrical contact between the connecting end of an implantable electrical lead and the electrical circuits within a sealed housing of an implantable medical device without sacrificing the integrity of the seal of the implantable medical device, said method comprising the steps of:
  (a) forming an indented channel in said housing, said channel having an open end at the surface of said housing for slidably receiving the connecting end of said electrical lead, said channel further having a closed end inside of said housing for preserving the integrity of the seal of said housing, said channel having a plurality of conductive coaxial cylindrical portions, the diameter of successive cylindrical portions decreasing from the open end to the closed end, and said channel also having at least one of the cylindrical portions thereof made from an electrically conductive material that is electrically isolated from the remainder of said housing, said electrically conductive portion having a front side that is accessible through the open indented channel, and a back side that is accessible from within the sealed housing;

(b) sliding the connecting end of said electrical lead into said channel such that at least one electrode on the connecting end of said lead is in electrical contact with said at least one electrically conductive portion of said indented channel;

(c) electrically connecting the back side of the electrically conductive portion of the indented channel to the electrical circuits within the sealed housing; and (d) sealing the indented channel to prevent entry of body fluids therein.

31. The method of claim 30 wherein step (d) of sealing the indented channel further includes the step of detachably locking the electrical lead within said indented channel.

32. The method of claim 31 wherein the step of detachably locking the electrical lead within said channel comprises gripping the electrical lead with a collar having a shrinking diameter.

* * * * *